(12) United States Patent
Jia et al.

(10) Patent No.: US 12,163,133 B2
(45) Date of Patent: Dec. 10, 2024

(54) USE OF MIR-132 AND MIR-212 IN PREPARATION OF DRUG FOR TREATING ADDICTION

(71) Applicant: Shenzhen Kangning Hospital (Shenzhen Mental Health Institute, Shenzhen Mental Health Center), Shenzhen (CN)

(72) Inventors: Xiaojian Jia, Shenzhen (CN); Han Rong, Shenzhen (CN); Mei Yang, Shenzhen (CN); Huiming Liu, Shenzhen (CN); Tiebang Liu, Shenzhen (CN)

(73) Assignee: Shenzhen Kangning Hospital (Shenzhen Mental Health Institute Shenzhen Mental Health Center), Shenzhen (CN)

( * ) Notice: Subject to any disclaimer, the term of this patent is extended or adjusted under 35 U.S.C. 154(b) by 998 days.

(21) Appl. No.: 17/151,667

(22) Filed: Jan. 19, 2021

(65) Prior Publication Data

US 2021/0230605 A1    Jul. 29, 2021

Related U.S. Application Data

(63) Continuation of application No. PCT/CN2020/089294, filed on May 9, 2020.

(30) Foreign Application Priority Data

Jul. 5, 2019   (CN) .......................... 201910602192.6
Jul. 5, 2019   (CN) .......................... 201910602193.0

(51) Int. Cl.
| | | |
|---|---|---|
| *C12Q 1/68* | (2018.01) | |
| *A61P 25/30* | (2006.01) | |
| *C12N 5/079* | (2010.01) | |
| *C12N 15/113* | (2010.01) | |
| *C12N 15/67* | (2006.01) | |
| *C12Q 1/6809* | (2018.01) | |
| *C12Q 1/6876* | (2018.01) | |

(52) U.S. Cl.
CPC .......... *C12N 15/1138* (2013.01); *A61P 25/30* (2018.01); *C12N 2310/141* (2013.01); *C12N 2310/531* (2013.01)

(58) Field of Classification Search
CPC ........ C12Q 2600/158; C12Q 2600/178; C12Q 2525/207; C12N 15/85; C12N 5/0619
See application file for complete search history.

(56) References Cited

U.S. PATENT DOCUMENTS

| | | |
|---|---|---|
| 2006/0057185 A1 | 3/2006 | Akimoto |
| 2009/0149823 A1 | 6/2009 | Orgill et al. |
| 2014/0080894 A1 | 3/2014 | Mcelligott |

FOREIGN PATENT DOCUMENTS

| | | |
|---|---|---|
| CN | 105624195 A | 6/2016 |
| CN | 105755027 A | 7/2016 |
| CN | 105861532 A | 8/2016 |
| CN | 110200986 A | 9/2019 |
| CN | 110279707 A | 9/2019 |

OTHER PUBLICATIONS

Internation Search Report of PCT/CN2020/089294, Mailed Jul. 29, 2020.

*Primary Examiner* — Barry A Chestnut
(74) *Attorney, Agent, or Firm* — True Shepherd LLC; Andrew C. Cheng

(57) ABSTRACT

The disclosure provides a non-therapeutic method for regulating DAT gene expression in a cell, which includes the step of increasing or decreasing an amount of a miR-132/212 in the cell; further provides a use of the above miRNA, an enhancer thereof or an attenuator thereof in preparing a drug for regulating uptake of dopamine by a cell; and an application of the above miRNA, the enhancer thereof or the attenuator thereof in preparing a drug for treating psychoactive substance addiction.

9 Claims, 11 Drawing Sheets
Specification includes a Sequence Listing.

```
Hsa  UGACUGUUUACACC. UU. UCC
Ptr  UGACUGUUUACACC. UU. UCC
Mml  UGACUGUUUACACC. UU. UCC
Oga  CGACUGUUUACACCCUU. UCU
Mmu  UGACUGUUCACACC. CAAUCC
Rno  UGACUGUUCACACC. CAAAUC
Dno  UGACUGUUUACACA. UG. UCC
```

FIG. 1

```
                                         7mer-m8
SLC6A3 3' UTR (155-161)   5' ...AGACUCCUCUCUUCUGACUGUUU...
                                              | | | | | | |
        hsa-miR-132       3'     GCUGGUACCGACAUCUGACAAU 7mer-m8
SLC6A3 3' UTR (155-161)   5' ...AGACUCCUCUCUUCUGACUGUUU...
                                              | | | | | | |
        hsa-miR-212       3'     CCGGCACUGACCUCUGACAAU
```

FIG. 2

SEQUENCE LISTING

```
<160> NUMBER OF SEQ ID NOS: 8

<210> SEQ ID NO 1
<211> LENGTH: 19
<212> TYPE: RNA
<213> ORGANISM: Homo sapiens

<400> SEQUENCE: 1
```

```
ugacuguuua caccuuucc                                                    19

<210> SEQ ID NO 2
<211> LENGTH: 20
<212> TYPE: RNA
<213> ORGANISM: Otolemur garnetti

<400> SEQUENCE: 2
cgacuguuua cacccuuucu                                                   20

<210> SEQ ID NO 3
<211> LENGTH: 20
<212> TYPE: RNA
<213> ORGANISM: Microcebus murinus

<400> SEQUENCE: 3
ugacuguuca cacccaaucc                                                   20

<210> SEQ ID NO 4
<211> LENGTH: 20
<212> TYPE: RNA
<213> ORGANISM: Rattus norvegicus

<400> SEQUENCE: 4
ugacuguuca cacccaaauc                                                   20

<210> SEQ ID NO 5
<211> LENGTH: 19
<212> TYPE: RNA
<213> ORGANISM: Dasypus novemcinctus

<400> SEQUENCE: 5
ugacuguuua cacaugucc                                                    19

<210> SEQ ID NO 6
<211> LENGTH: 23
<212> TYPE: RNA
<213> ORGANISM: Homo sapiens

<400> SEQUENCE: 6
agacuccucu cuucugacug uuu                                               23

<210> SEQ ID NO 7
<211> LENGTH: 22
<212> TYPE: RNA
<213> ORGANISM: Homo sapiens

<400> SEQUENCE: 7
uaacagucua cagccauggu cg                                                22

<210> SEQ ID NO 8
<211> LENGTH: 21
<212> TYPE: RNA
<213> ORGANISM: Homo sapiens

<400> SEQUENCE: 8
uaacagucuc cagucacggc c                                                 21
```

USE OF MIR-132 AND MIR-212 IN PREPARATION OF DRUG FOR TREATING ADDICTION

CROSS-REFERENCE TO RELATED APPLICATIONS

This application is a continuation of International Patent Application No. PCT/CN2020/089294 with a filing date of May 9, 2020, designating the United States, now pending, and further claims priority to Chinese Patent Application No. 201910602193.0 with a filing date of Jul. 5, 2019 and Chinese Patent Application No. 201910602192.6 with a filing date of Jul. 5, 2019. The content of the aforementioned applications, including any intervening amendments thereto, are incorporated herein by reference.

CROSS-REFERENCE TO A SEQUENCE LISTING

This application includes a Sequence Listing submitted electronically as a text file named SEQ-list.txt, created on Apr. 2, 2021, with a size of 1,559 bytes. The Sequence Listing is incorporated by reference herein.

TECHNICAL FIELD

The disclosure relates to the fields of molecular biology and medicine, and more particularly, to use of a miR-132 and a miR-212 in preparing a drug for treating psychoactive substance addiction.

BACKGROUND OF THE PRESENT INVENTION

As a brain dysfunction caused by use of psychoactive substances, psychoactive substance addiction makes people lose control to the use of these substances. The psychoactive substance addiction is a chronic recurrent disease usually associated by other mental and physical disorders, including classical symptoms such as uncontrollable drug administration and withdrawal syndrome.

The neurotransmitter dopamine (DA) controls a plurality of functions including movement, cognition, emotion, reward, or the like. A large number of neuropharmacological evidences from human and animals show that a DA system plays an important role in three stages of an addiction cycle: a binge stage, a withdrawal stage and a craving stage). It is a normal mechanism that by reuptake the DA is transferred from a synaptic cleft through a presynaptic membrane to a presynaptic neuron. Interruption of DA signals is usually achieved through a dopamine transporter (DAT)-mediated cell membrane sodium-dependent reuptake process, which plays a crucial role in maintenance of neuron DA homeostasis. One important mechanism of the psychoactive substances is blocking the reuptake of the DA released from a presynaptic terminal. A normal biological effect of the DA is amplified through the blockage of reuptake.

These substances directly affect DAT in two ways. One way is DA uptake blocking, as with cocaine and methylphenidate, through binding with DAT, thereby inhibiting the transport of the DA. The other way is replacing DA as a substrate for DAT and translocating into a cell, as with benzedrine and methylamphetamine, which trigger release of the DA stored in the cell to a synaptic cleft. Opioids indirectly influence a DA level in the synaptic cleft, act on opioid receptors, and block the inhibitory effects of γ-aminobutyric acid (GABA) neurons on dopaminergic neurons, resulting in release of a large amount of DA from the presynaptic membrane to the synaptic cleft. No matter which pathway works, these substances elevate the DA level in the synaptic cleft, which acts on a DA receptor on the presynaptic membrane, enhancing the DA signal, thus resulting in a series of drug reactions.

The DAT is a membrane protein located in the terminal of the central dopaminergic neuron, and is a member of a $Na^+/Cl^-$-dependent transporter gene family. The SLC6A3 gene encoding the DAT is located at a chromosome 5p15.32, which spans 60 kb, contains 15 exons and encodes 620 amino acids. DAT is inferred to have 12 transmembrane domains, one extracellular ring structure and several N-terminal glycosylation sites. The DAT needs to be glycosylated first, so as to have a function of transporting the DA.

MiRNAs are post-transcriptional regulators of gene expression, which play an important role in a plurality of cell processes. In a variety of diseases, such as cancer, cardiovascular disease, acquired immunodeficiency syndrome, drug addiction, a change of an miRNA expression profile affects an interaction between the miRNA and a target thereof. Increasing evidences suggest chronic abuse of psychotropic substance can alter the miRNA expression profile.

Therefore, if a miRNA capable of regulating DAT gene expression can be found, it is possible to control the cell uptake of the DAT based on the miRNA, and effective methods and drugs for drug addiction treatment can be developed.

SUMMARY OF PRESENT INVENTION

In the process of research, the inventors found out the binding sites of mir-212 (hsa-miR-212-3p, MIMAT0000269) and mir-132 (hsa-miR-132-3p, MIMAT0000426) exists in a 3'UTR of an SLC6A3 gene.

Based on the above findings, the disclosure provides a non-therapeutic use of miR-132 and/or miR-212 in regulating DAT gene expression in a cell.

The disclosure further provides a non-therapeutic method for regulating DAT gene expression in a cell, which includes a step of increasing or decreasing an amount of miR-132 and/or a miR-212 in the cell.

In a specific embodiment, the increasing the amount of miR-132 and/or miR-212 in the cell is implemented by introducing a miR-132 enhancer and/or a miR-212 enhancer into the cell.

In another specific embodiment, the decreasing the amount of miR-212 and/or miR-132 in the cell is implemented by introducing a miR-132 attenuator and/or a miR-212 attenuator into the cell.

In a specific embodiment, the cell is a cell expressing a DAT gene.

In a specific embodiment, the DAT gene is a SLC6A3 gene or a homologous gene thereof.

In a specific embodiment, the cell is a mammalian nerve cell.

The disclosure further provides a use of an miR-132, a miR-132 enhancer, an miR-132 attenuator, an miR-212, an miR-212 enhancer or an miR-212 attenuator in preparing a drug for regulating uptake of dopamine by a cell.

In a preferred embodiment, the cell is a mammalian nerve cell.

The disclosure further provides a use of an miR-132, an miR-132 enhancer, an miR-132 attenuator, an miR-212, an miR-212 enhancer or an miR-212 attenuator in preparing a drug for psychoactive substance addiction.

DESCRIPTION OF THE DRAWINGS

FIG. 1 is a partial alignment of a 3'UTR of an SLC6A3 mRNA in a mammal, wherein Hsa refers to *Homo sapiens* (SEQ ID NO: 1); Ptr refers to *Pan troglodytes* (SEQ ID NO: 1); Mml refers to *Macaca* mulatta (SEQ ID NO:1); Oga refers to *Otolemur garnetti* (SEQ ID NO:2); Mmu refers to *Mus musculus* (SEQ ID NO:3); Rno refers to *Rattus norvegicus* (SEQ ID NO:4); and Dno refers to *Dasypus novemcinctus* (SEQ ID NO:5);

FIG. 2 is a sequence matching of binding sites of miR-132/212 deduced in a 3'UTR of an SLC6A3 with miR-132 and miR-212 respectively;

DETAILED DESCRIPTION OF PREFERRED EMBODIMENTS

The following describes the principles and features of the disclosure with reference to the accompanying drawings, and the examples are only used to explain the disclosure, but are not intended to limit the scope of the claims.

Term Explanation 1) miRNA enhancer: a nucleic acid substance that increases an amount of a corresponding miRNA in a cell, such as an miRNA mimic, an miRNA expression vector driven by a strong promoter, or the like.

2) miRNA attenuator: a nucleic acid substance that decreases an amount of a corresponding miRNA in a cell, such as an miRNA inhibitor, an miRNA-sponge, or the like.

3) miRNA-sponge: a single-stranded RNA with a plurality of tandem repeats, wherein each repeating unit has a complementary sequence of all or part of sequences of a corresponding miRNA, so that the miRNA-sponge can bind and absorb the corresponding miRNA and reduce an effective concentration of the miRNA in a cell.

1. Study on 3'UTR of SLC6A3 mRNA

The sequence of a 3'UTR of a SL (6A3 mRNA (SEQ ID NO:6) was analyzed carefully, which had a length of 1945 bp. After aligning homologous sequences of SI (6A3 genes from multiple species, it was found that bases at sites 153-159 of the 3'UTR of the SLC6A3 mRNA (SEQ ID NO: 1 to SEQ ID NO:5) in a mammal were highly conserved (FIG. 1), and sequences thereof were accurately matched with sites 2-8 of mature miR132 (SEQ ID NO: 7) and mature miR-212 (SEQ ID NO:8) (FIG. 2). It suggested that these sites might be binding sites of miR132 and miR-212. MiR132 and miR-212 might regulate SI. (6A3 gene expression, and then regulate cell uptake of DA.

2. Regulation of miR132 and miR-212 on DAT Gene Expression in Nerve Cells

In order to study regulation of miR132 and miR-212 in a nerve cell on DAT expression, miR132 and miR-212 mimics and inhibitors were transiently transfected into a SK-N-SH cell, respectively. 48 hours later, the expression level of SLC6A3 mRNA was detected through real-time PCR, and a DAT protein level was detected through western blotting.

Figure 3:
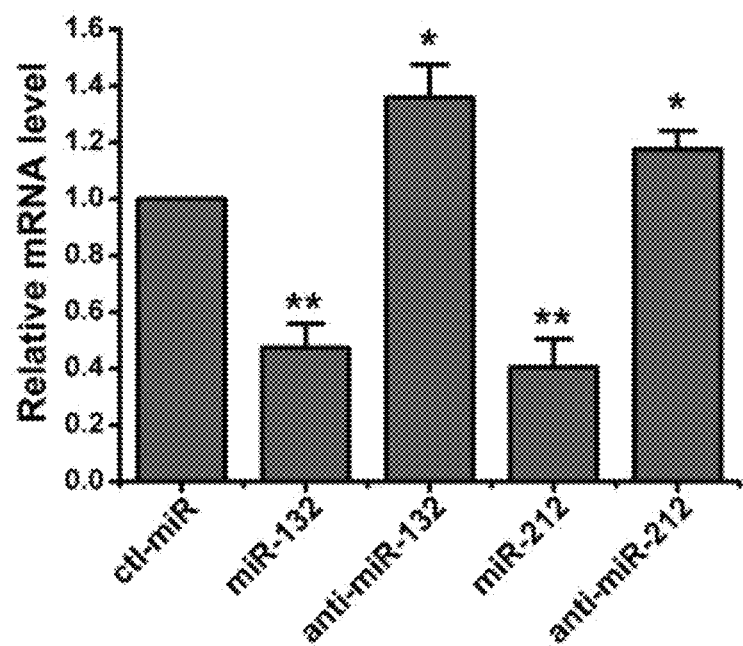
FIG. 3 shows effects of miR-132 and miR-212 in an SK-N-SH cell on an expression level of an SLC6A3 mRNA.
Figure 4:
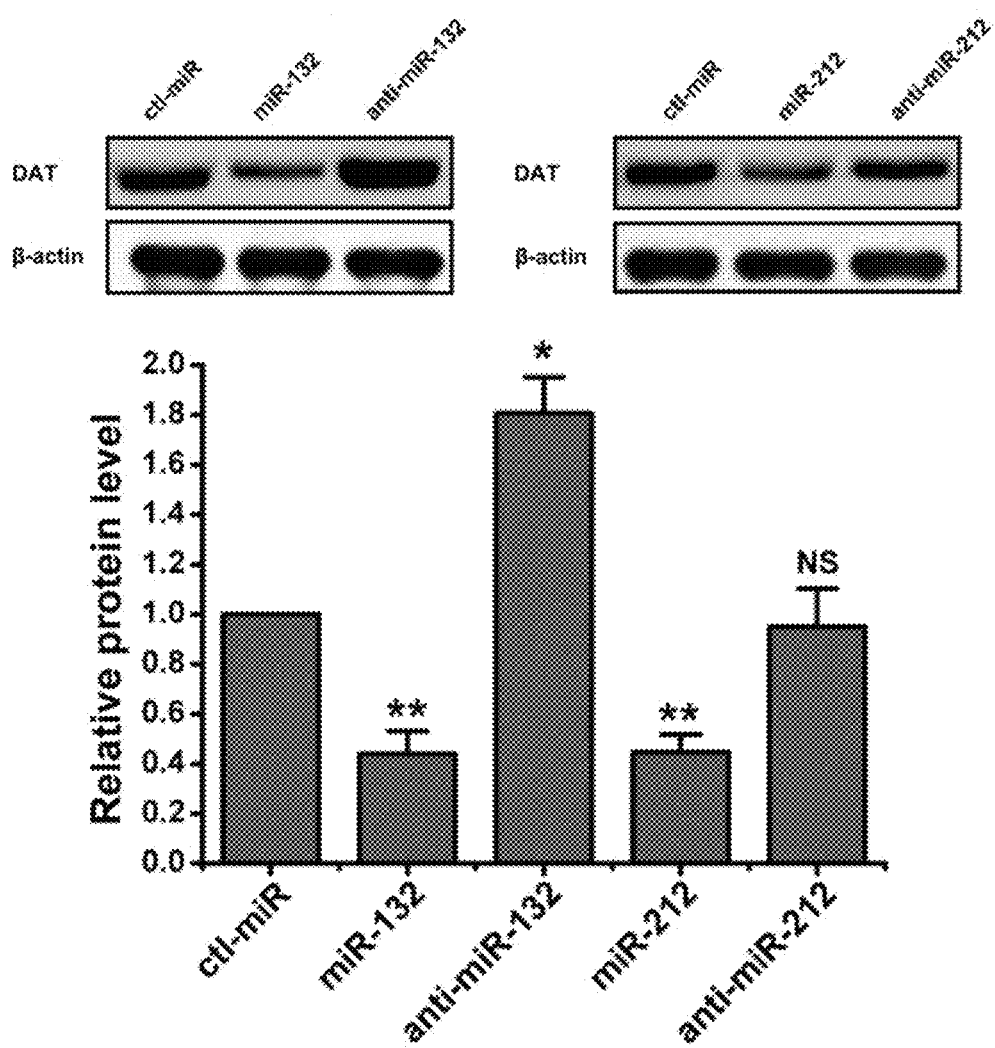
FIG. 4 is a western blotting graph of a DAT protein and a quantitative statistical diagram obtained according to the western blotting graph.

The results showed that in the SK-N-SH cell, the miR-132 mimic caused a significant decrease of the SI (6A3 mRNA expression level by 52.7%, the miR-132 inhibitor caused a significant increase of the SI. (6A3 mRNA expression level by 36.0%, the miR-212 mimic caused a significant decrease of the SI. (6A3 mRNA expression level by 59.7%, and the miR-212 inhibitor caused a significant increase of the SL (6A3 mRNA expression level by 17.7% (FIG. 3). The changes of DAT protein expression level was similar to that of the SLC643 mRNA expression level: the miR-132 mimic caused a significant decrease of the DAT protein expression by 56.0% and 55.4%; the miR-132 inhibitor significantly increased the DAT protein expression by 80.8%, and the miR-212 mimic significantly decreased the DAT protein expression by 55.4% (FIG. 4). This indicated that the miR-132 and the miR-212 could affect the mRNA expression and the DAT protein expression in the SK-N-SH cell.

3. Confirmation of Binding Site of miR-132/212 in SL (6A3 3'UTR

Figure 5:
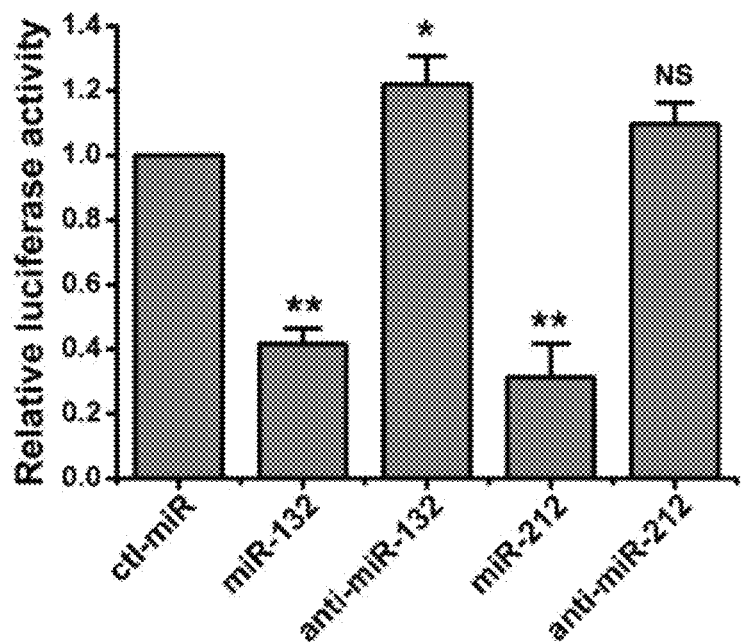
FIG. 5 shows effects of miR-132 and miR-212 on an activity of a luciferase reporter construct containing a wild-type 3'UTR of an SLC6A3.
Figure 6:
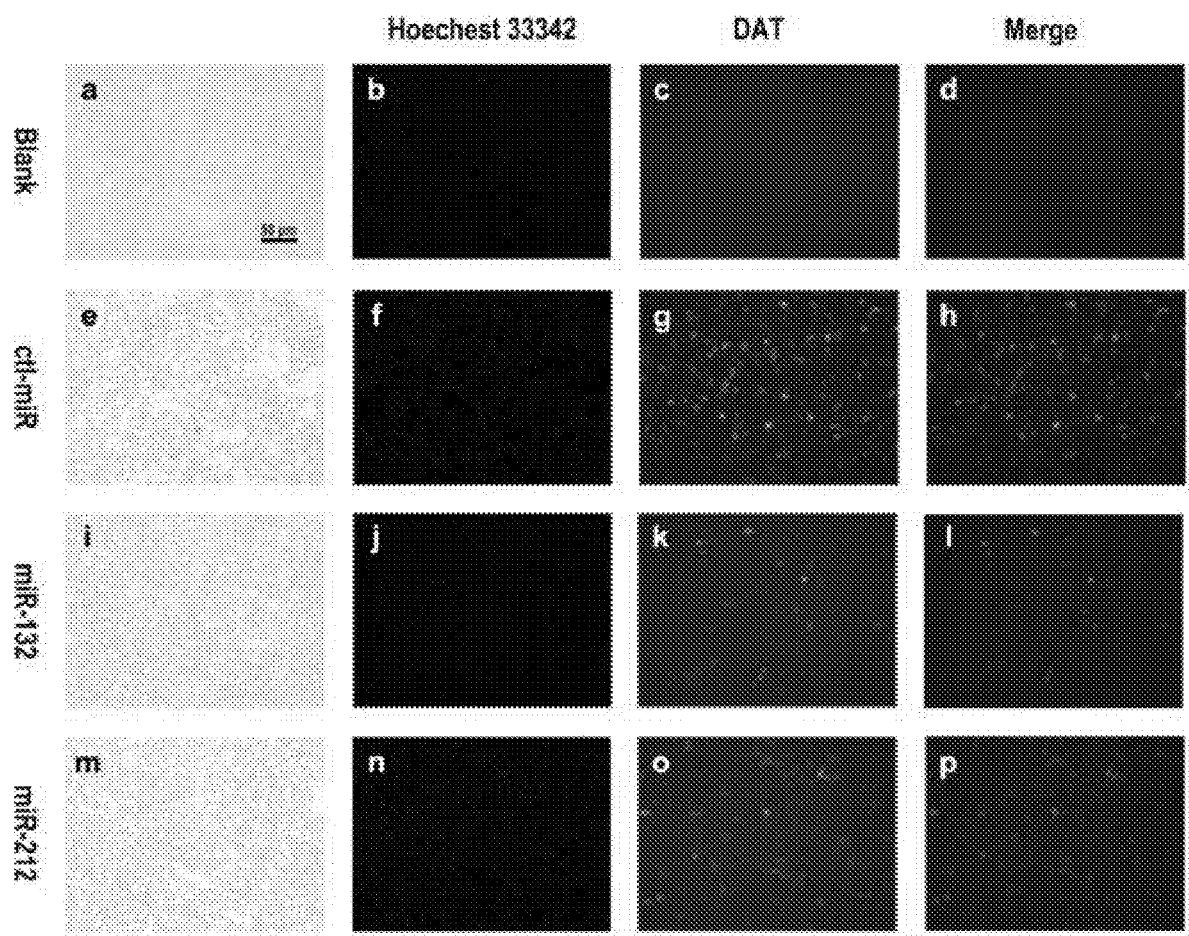
FIG. 6 is a fluorescence microphotograph of a HepG2 transfected with a DAT-GFP fusion-expression plasmid and a corresponding miRNA.

The 3'UTR fragment of SI. (6A3 was inserted into a downstream of psiCHECK2 vector *renilla* luciferase reporter gene to obtain a luciferase reporter gene expression vector. Experiments proved that the luciferase reporter gene expression plasmid and a miRNA were transfected into a SK-N-SH cell through transient transfection, a *renilla* luciferase activity was detected after incubation for 24 hours, and a firefly luciferase was used for activity homogenization. The results showed that the miR-132 significantly decreased the luciferase activity in the SK-N-SH cell by 58.3%, and the inhibitor thereof increased the luciferase activity by 22.0%; the miR-212 significantly decreased the luciferase activity in the SK-N-SH cell by 68.7%, and the inhibitor thereof increased the luciferase activity by 9.7% (FIG. 5). The DAT coding sequence and 3'UTR were inserted into a downstream of a GFP gene to construct a GFP-DAT fusion expression plasmid. The plasmid was co-transfected with the miRNA into a HepG2 cell, and results were shown in FIG. 6. The miR-132 and the miR-212 both significantly reduced GFP-DAT fusion protein expression. Thus, it could be seen that action sites of the miR-132 and the miR-212 were both located on the 3'UTR of the SLC6A3.

Figure 7:
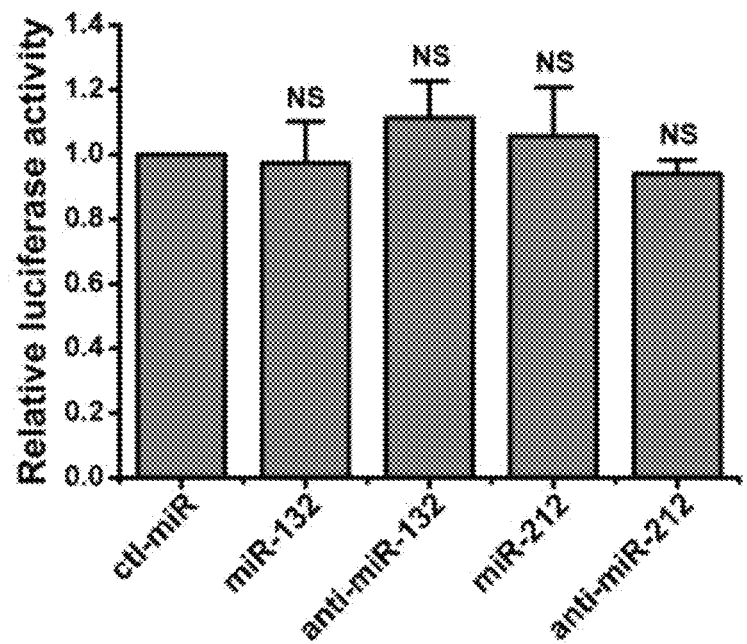
FIG. 7 shows effects of miR-132 and miR-212 on an activity of a luciferase reporter construct containing a 3'UTR of an SLC6A3 mutated in an miR-132/212 seed region.

Bases at sites 153-159 of the 3'UTR of the SLC6A3 mRNA were mutated, the mutated 3'UTR of the SL (6A3 was inserted into the downstream of the *renilla* luciferase reporter gene of the plasmid psiCHECK2 to obtain a mutated luciferase reporter gene expression plasmid. Then the mutated luciferase reporter gene expression plasmid and a miRNA were transfected into a SK-N-SH cell. Results showed that none of miR-132, miR-212, and the inhibitors of miR-132 and miR-212 affected the activity of the *renilla* luciferase (FIG. 7). The results indicated that the sites 153-159 of SL (6A3 3'UTR were action sites of the miR-212.

4. Effects of Mir-132 and miR-212 on Dopamine Uptake of in Nerve Cell

Figure 8:
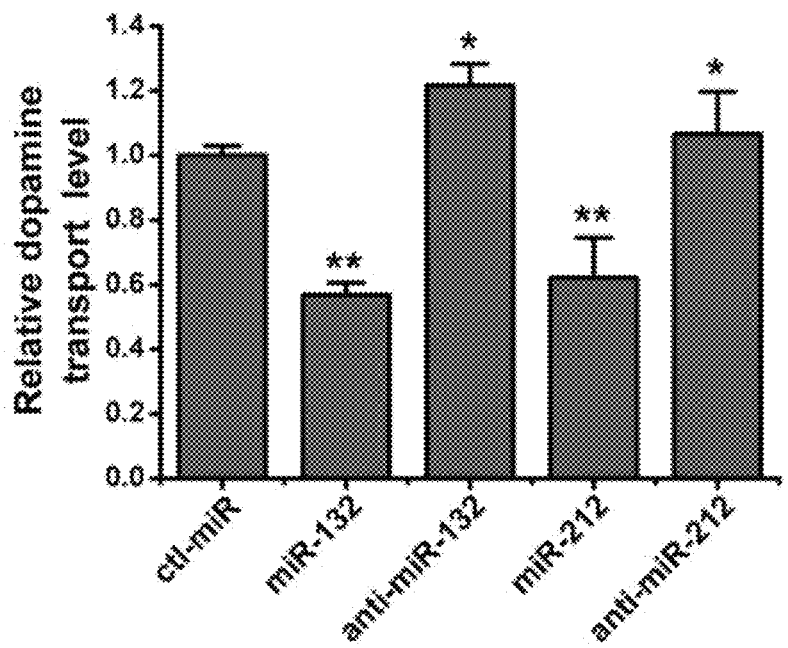
FIG. 8 shows effects of miR-132 and miRNA-212 on uptake of DA by an SK-N-SH cell.

A miRNA was transfected into a SK-N-SH nerve cell, and 48 hours later, incubated in a medium containing 5 μg/ml DA for 5 hours. Then, The DA level in the cell was detected. Experimental results showed that the miR-132 significantly decreased the uptake of the DA by the SK-N-SH nerve cell by 43.1%, and the inhibitor thereof increased the uptake of the DA by the SK-N-SH nerve cell by 27.1%; the miR-212 significantly decreased the uptake of the DA by the SK-N-SH nerve cell by 37.9%, and the inhibitor thereof increased the uptake of the DA by the SK-N-SH nerve cell by 6.7% (FIG. 8).

Figure 9:
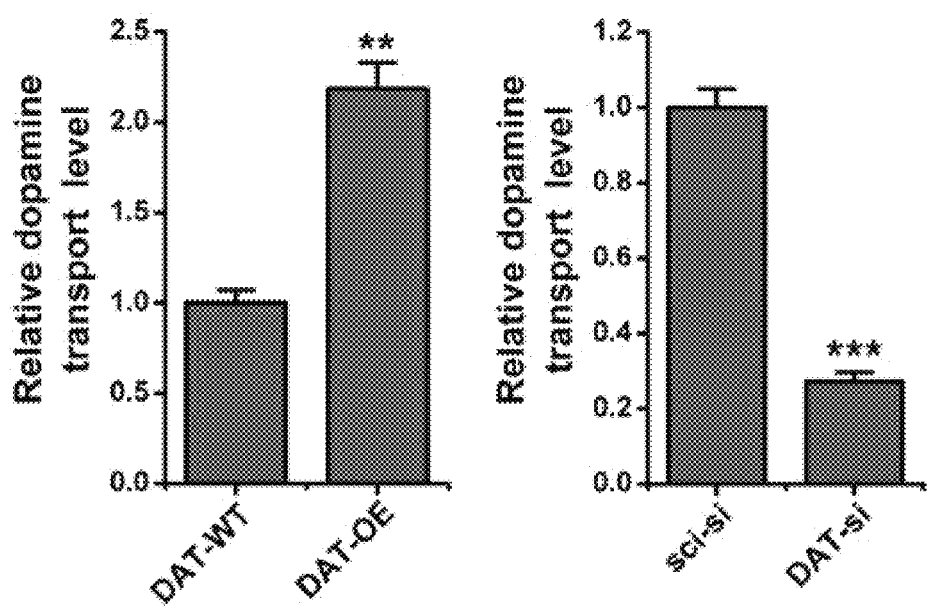
FIG. 9 is a statistical chart of a DAT expression quantity in an SK-N-SH cell, into which a DAT gene overexpression plasmid and an siRNA of a DAT gene are introducing.
Figure 10:
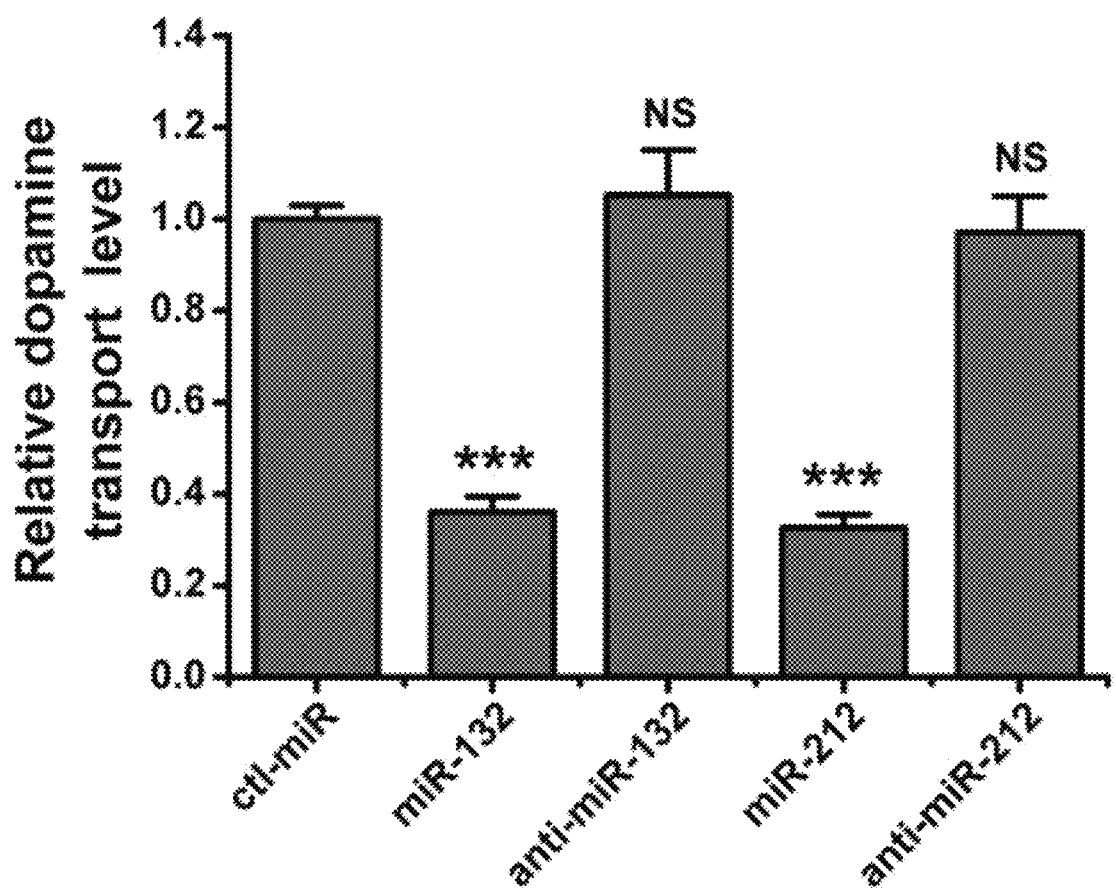
FIG. 10 shows effects of miR-132 and miRNA-212 on a DAT expression quantity in an SK-N-SH cell in which DAT gene is overexpressed.

Further, a gene overexpression experiment and a gene silencing experiment were carried out. A SK-N-SH cell was transfected with a plasmid pcDNA3.1-SL (6A3 to overexpress a DAT, and an expression quantity of the DAT was increased by 20 times, which resulted in increase of a DA content in the cell by 118.6%. A siRNA was transfected into the SK-N-SH cell, and the SI (6A3 mRNA was significantly decreased, resulting in significant decrease of the DA level in the cell by 72.8% (FIG. 9). The miR-132 significantly decreased the DA level in the SK-N-SH cell which overexpressed the DAT by 63.9%, and the miR-212 significantly decreased the DA level in the SK-N-SH cell which overexpressed the DAT by 67.4% (FIG. 10).

All the above experiments carried out on the SK-N-SH cells were carried out on another type of nerve cell SK-N-BE (2), and similar results were obtained (the results were not shown for the sake of simplicity), which indicated that the effects of the miR-132 and the miR-212 on the nerve cell were not only limited to the SK-N-SH nerve cell.

5. Effects of miR-132 and miR-212 on Conditioned Place Preference CPP of Rats

CPP is a response-enhancing model, which is used for assessing psychological dependence caused by a drug rewarding effect, and is also an effective tool widely used to study drug withdrawal behaviors.

Based on an established Morphine CPP rat model, one blank control group and four experimental groups were set up: lentivirus-control group (Lv-ctl), siRNA-sponge group (siRNA-sponge) and lentivirus-miR-132/212-sponge group (Lv-sponge), with 10 SD rats in each group. The miR-132/212 sponge included three mir-132 (hsa-miR-132-3p, MIMAT0000426) complementary binding regions and three miR-212 complementary binding regions.

The rats were anesthetized with isoflurane and placed on a heating plate, and syringe needles were adjusted to face towards a middle line at an angle of 16° to avoid passing through a lateral ventricle. Injection positions were respectively: 1.5 mm in front of a bregma, 3.8 mm adjacent to the middle line, and 6.6 mm perpendicular to a skull Plane. The rats were recovered for 5 days to 10 days after surgery and then used for follow-up experiments.

Corresponding injections were bilateral-delivered to each group for more than one minute: normal saline (1 μl), lentivirus control (1.2×1010 TU/ml, 1 μl), DAT-siRNA (1 mM, 1 μl), siRNA-sponge (equal mixture of 1 mm DAT-siRNA and 1.2×1010 TU/ml lentivirus-sponge, 1 μl) and lentivirus-sponge (1.2× 1010 TU/mL, 1 μl). Then, the syringe needles were left in place for one minute to allow the drugs to diffuse completely.

Figure 11:
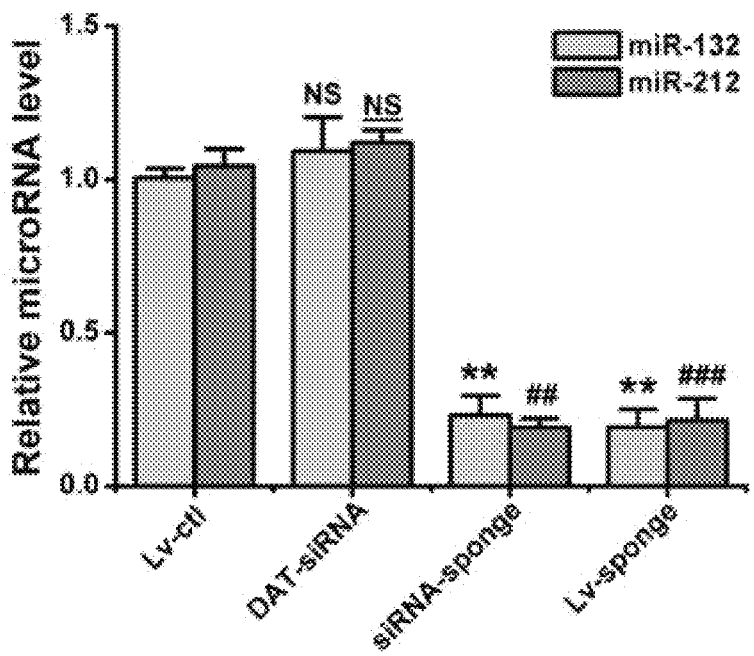
FIG. 11 shows miR-132 and miR-212 expression levels in an NAc of a Morphine CPP rat.
Figure 12:
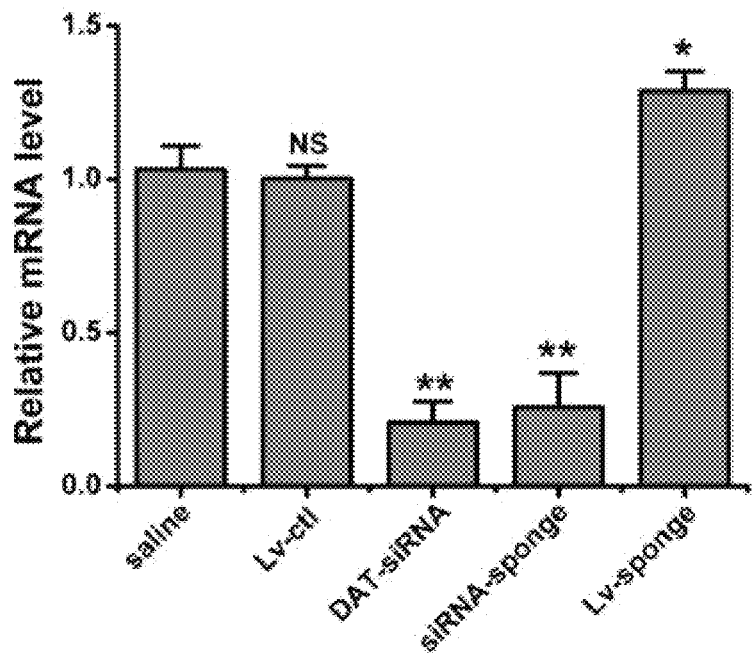
FIG. 12 shows an SLC6A3 mRNA expression level in an NAc of a Morphine CPP rat.
Figure 13:
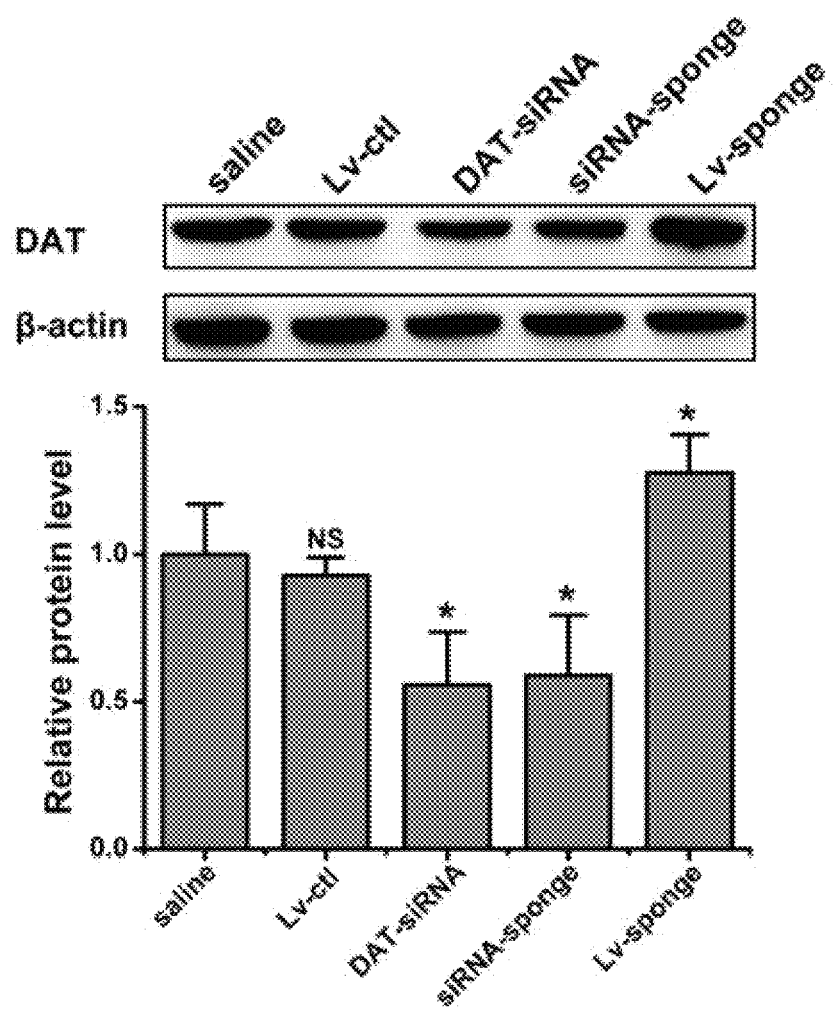
FIG. 13 shows a DAT expression level in an NAc of a Morphine CPP rat.
Figure 14:
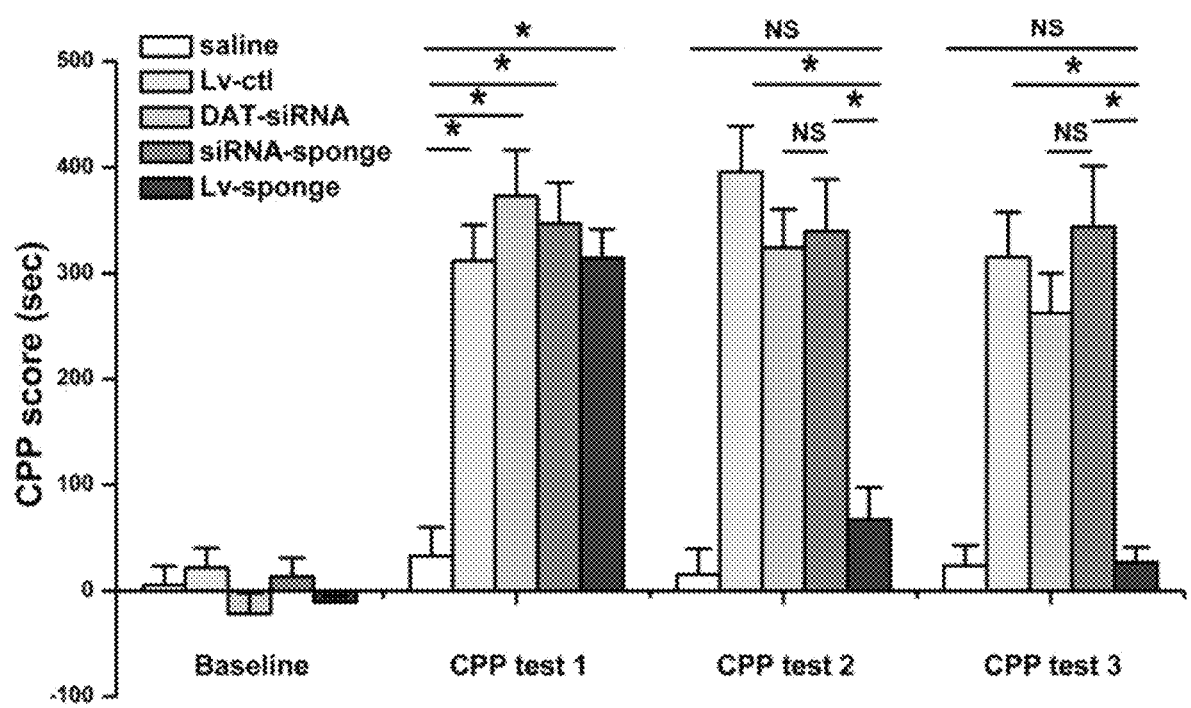
FIG. 14 shows CPP scores of different treatment groups on a 0th day (test 1), a 5th day (test 2) and a 10th day (test 3) after treatment.

Experimental results showed that compared with the blank control group (normal saline), the miR-132 and miR-212 expression levels of the siRNA-sponge group were significantly decreased by 77.0% and 80.9%, and the miR-132 and miR-212 expression levels of the Lv-sponge group were significantly decreased by 80.8% and 78.6% (FIG. 11). The mRNA level of the Lv-sponge group was significantly decreased by 28.8%, and the mRNA levels of the DAT-siRNA group and the siRNA-sponge group were significantly decreased by 79.3% and 74.3% (FIG. 12). The protein level of the Lv-sponge group was significantly decreased by 27.5%, and the protein levels of the DAT-siRNA group and the siRNA-sponge group were significantly decreased by 44.4% and 41.2% (FIG. 13). After treatment for 5 days or 10 days, The Morphine CPP of the Lv-sponge group was significantly lower than those of the DAT-siRNA group and the siRNA-sponge group, and no significant difference existed between the blank control group (normal saline) and the Lv-sponge group (FIG. 14).

The above results indicate that, in the rat CPP experiments, the miR-132/212 level in the NAc can increase the expression quantity of the DAT in the rats and decrease the Morphine CPP, which indicates that a substance decreasing the amount of the miR-132/212 can be used to prepare a drug for treating morphine addiction. Similar results have also been obtained in other psychoactive substance experiments.

The above is only a preferred embodiment of the disclosure, and is not intended to limit the disclosure. Any modifications, equivalent substitutions and improvements made without departing from the spirit and principle of the disclosure shall fall within the scope of protection of the disclosure.

We claim:

1. A non-therapeutic use of miR-132 and/or miR-212 in regulating DAT gene expression in a cell.

2. A non-therapeutic method for regulating DAT gene expression in a cell, comprising a step of increasing or decreasing an amount of miR-132 and/or miR-212 in the cell.

3. The method according to claim 2, wherein increasing the amount of miR-132 and/or miR-212 in the cell is implemented by introducing an miR-132 enhancer and/or an miR-212 enhancer into the cell.

4. The method according to claim 2, wherein decreasing the amount of miR-132 and/or miR-212 in the cell is implemented by introducing an miR-132 attenuator and/or a miR-212 attenuator into the cell.

5. The method according to claim 2, wherein the cell is a cell expressing a DAT gene.

6. The method according to claim 5, wherein the DAT gene is SLC6A3 gene or a homologous gene thereof.

7. The method according to claim 6, wherein the cell is a mammalian nerve cell.

8. A use of miR-132, an miR-132 enhancer, an miR-132 attenuator, miR-212, an miR-212 enhancer or a miR-212 attenuator in preparing a drug for regulating uptake of dopamine by a cell or a drug for treating psychoactive substance addiction.

9. The use according to claim 8, wherein the cell is a mammalian nerve cell.

* * * * *